US012670604B2

(12) United States Patent
Han et al.

(10) Patent No.: US 12,670,604 B2
(45) Date of Patent: Jun. 30, 2026

(54) METHOD AND APPARATUS FOR EVELUATING HEALTH CONDITION BY USING SKELETON MODEL

(71) Applicants: ROWAN Inc., Seoul (KR); AJOU UNIVERSITY INDUSTRY-ACADEMIC COOPERATION FOUNDATION, Suwon-si (KR); INHA UNIVERSITY RESEARCH AND BUSINESS FOUNDATION, Incheon (KR)

(72) Inventors: Seung Hyun Han, Goyang-si (KR); Young Uk Park, Seoul (KR); Mun Cheong Choi, Hanam-si (KR); So Young Moon, Seoul (KR); Seong Hye Choi, Seoul (KR); Hong Sun Song, Guri-si (KR)

(73) Assignees: ROWAN Inc., Seoul (KR); AJOU UNIVERSITY INDUSTRY-ACADEMIC COOPERATION, Suwon-si (KR); INHA UNIVERSITY RESEARCH AND BUSINESS FOUNDATION, Incheon (KR)

( * ) Notice: Subject to any disclaimer, the term of this patent is extended or adjusted under 35 U.S.C. 154(b) by 125 days.

(21) Appl. No.: 18/665,455

(22) Filed: May 15, 2024

(65) Prior Publication Data
US 2024/0303834 A1    Sep. 12, 2024

Related U.S. Application Data

(63) Continuation of application No. PCT/KR2022/017839, filed on Nov. 14, 2022.

(30) Foreign Application Priority Data

Nov. 23, 2021    (KR) ........................ 10-2021-0162426

(51) Int. Cl.
*G06T 7/246* (2017.01)
*A61B 5/00* (2006.01)
(Continued)

(52) U.S. Cl.
CPC ............ *G06T 7/251* (2017.01); *A61B 5/1128* (2013.01); *A61B 5/742* (2013.01); *G06T 7/0014* (2013.01);
(Continued)

(58) Field of Classification Search
CPC . G06T 2207/30004; G06T 2207/30196; G06T 2207/30241; G06T 7/0014; G06T 7/0016; G06T 7/248; G06T 7/251
See application file for complete search history.

(56) References Cited

U.S. PATENT DOCUMENTS

2017/0043215 A1* 2/2017 Peterson ................ G06V 40/23
2019/0340431 A1* 11/2019 Wang ...................... G06F 18/22
(Continued)

FOREIGN PATENT DOCUMENTS

KR    10-2016-0116677 A    10/2016
KR         101970687 B1    4/2019
(Continued)

OTHER PUBLICATIONS

International Search Report of PCT/KR2022/017839, issued Mar. 6, 2023.
(Continued)

*Primary Examiner* — Ming Wu
(74) *Attorney, Agent, or Firm* — ZION IP; Byungwoong Park

(57) ABSTRACT

A method, performed by a health management server, for evaluating a health condition by using a skeleton model. In detail, the method comprises the steps of: providing, to a user apparatus, a standard motion image of a trainer per-
(Continued)

forming a standard motion; receiving, from the user apparatus, a user motion image of a user motion performed by a user following the standard motion; calculating a similarity between the standard motion and the user motion by comparing the standard motion image with the user motion image; and evaluating a health condition of the user on the basis of the calculated similarity.

7 Claims, 14 Drawing Sheets

(51) Int. Cl.
    *A61B 5/11*        (2006.01)
    *G06T 7/00*       (2017.01)

(52) U.S. Cl.
    CPC .... *G06T 7/248* (2017.01); *G06T 2207/30004* (2013.01); *G06T 2207/30196* (2013.01); *G06T 2207/30241* (2013.01)

(56)        References Cited

U.S. PATENT DOCUMENTS

2020/0402638 A1\*  12/2020  Song ........................ G06N 3/02
2021/0027485 A1\*   1/2021  Zhang ................... G06Q 50/12

FOREIGN PATENT DOCUMENTS

| KR | 102123869 | B1 | 6/2020 |
|----|-----------|----|--------|
| KR | 1020200073765 | A | 6/2020 |
| KR | 1020200144991 | A | 12/2020 |
| KR | 1020210017462 | A | 2/2021 |
| WO | 2019187099 | A1 | 10/2019 |

OTHER PUBLICATIONS

The extended European search report issued on Sep. 30, 2025.
Bruce X.B. Yu et al., "Skeleton-based human action evaluation using graph convolutional network for monitoring Alzheimer's progression", Jun. 9, 2021.

\* cited by examiner

METHOD AND APPARATUS FOR EVELUATING HEALTH CONDITION BY USING SKELETON MODEL

TECHNICAL FIELD

Embodiments relate to a method and device for evaluating health status. More particularly, embodiments relate to a method and device for evaluating cognitive impairment and exhaustion of physical strength by comparing motion information between a skeleton model of a standard motion model and a user's skeleton model.

BACKGROUND ART

As noncontact cultures spread, there is a growing need for remote medical care. For clinical determination of nervous system related diseases such as cognitive impairment, it is necessary to see users' actions with the naked eye, but the decline in hospital visits reduces examination and treatment.

On the other side, noncontact cultures contribute to the prevalence of training at home without going to gyms and related industry is growing fast. Home training services with improved quality provide a diverse selection of exercises and motivation to continue exercising, but as described above, there is no service for determination of nervous system diseases instead of hospital visit.

To solve this problem, there is a need for services to check the health status by sending images of motions for the determination of nervous system related diseases from each home to medical institutions.

(Related Art Document 1) Korean Patent Publication No. 10-2020-0073765 (2020 Jun. 24)

SUMMARY

Technical Problem

An object of the present disclosure is to evaluate a user's motor imitation by comparing a user motion with a standard motion.

An object of the present disclosure is to evaluate the user's cognitive impairment or exhaustion of physical strength by comparing the user motion with the standard motion.

An object of the present disclosure is to compare the user motion with the standard motion using skeleton models of the two motions.

An object of the present disclosure is to achieve rapid clinical determination by allowing motions of a plurality of users and their analysis results to be viewed on one display.

An object of the present disclosure is to determine similarity between the two motions more accurately by applying weights to the main body parts for each standard motion.

The problems to be solved by the present disclosure are not limited to the above-described problems, and may be extended to various matters that can be derived by the following embodiments of the present disclosure.

Technical Solution

A method for evaluating health status using skeleton models according to an embodiment of the present disclosure is performed by a health management server, and the method includes the steps of providing a user device with a standard motion image of a trainer making a standard motion, receiving a user motion image for a user motion of a user imitating the standard motion from the user device, calculating a similarity between the standard motion and the user motion by comparing the user motion image with the standard motion image, and evaluating the health status of the user based on the calculated similarity.

In an embodiment, the step of calculating the similarity may include the steps of acquiring a trainer skeleton motion model for the trainer making the standard motion in the standard motion image, acquiring a user skeleton motion model for the user making the user motion in the user motion image, and calculating the similarity by comparing feature points for each corresponding body part between the trainer skeleton motion model and the user skeleton motion model, wherein the feature points for each body part are nodes of the skeleton motion models.

In an embodiment, the step of calculating the similarity by comparing the feature points for each body part may include the steps of fetching a weight per body part for the standard motion from a database, and applying the weight per body part to the similarity calculation.

In an embodiment, the step of evaluating the health status may include evaluating exhaustion of physical strength or cognitive impairment level of the user, and the cognitive impairment level may be evaluated based on behavior feature data in cognitive impairment for each standard motion.

In an embodiment, the exhaustion of physical strength may be determined based on a sum of movement trajectories of the feature points for each body part of the user skeleton motion model; and a predefined physical strength exhaustion evaluation weight for an amount of movement for each body part.

In an embodiment, the method may include the steps of receiving the user motion image for each of a plurality of users from a plurality of user devices, displaying the plurality of received user motion images on a display device, calculating the similarity between each of the plurality of user motions in the plurality of received user motion images and the standard motion, and highlighting at least one of the plurality of user motion images displayed on the display device based on the calculated similarity.

In an embodiment, the step of highlighting may include highlighting a predetermined number of user motion images having the calculated similarity in a lower or higher range than a predetermined criterion among the plurality of user motion images.

In an embodiment, the step of highlighting may include the steps of calculating the similarity between users by comparing the skeleton motion models for the plurality of user motions, grouping the plurality of user motion images based on the calculated similarity between users, and differently displaying the grouped user motion images.

In an embodiment, the step of calculating the similarity between users by comparing the skeleton motion models for the plurality of user motions may include not applying the weight per body part for the standard motion.

A program stored in a computer-readable recording medium according to an embodiment of the present disclosure may include instructions for performing the above-described method.

Advantageous Effects

The present disclosure may evaluate the user's motor imitation by comparing the user motion with the standard motion.

The present disclosure may evaluate cognitive impairment or exhaustion of physical strength of the user by comparing the user motion with the standard motion.

The present disclosure may compare the user motion with the standard motion using the skeleton models of the two motions.

The present disclosure may achieve rapid clinical determination by allowing motions of a plurality of users and their analysis results to be viewed on one display.

The present disclosure may determine the similarity between the two motions more accurately by applying the weights to the main body parts for each standard motion.

It should be understood that the effects of the present disclosure are not limited to the above-described effects, and may be extended to various matters that can be derived from the following description of the embodiments of the present disclosure.

DETAILED DESCRIPTION OF EXEMPLARY EMBODIMENTS

Figure 1:
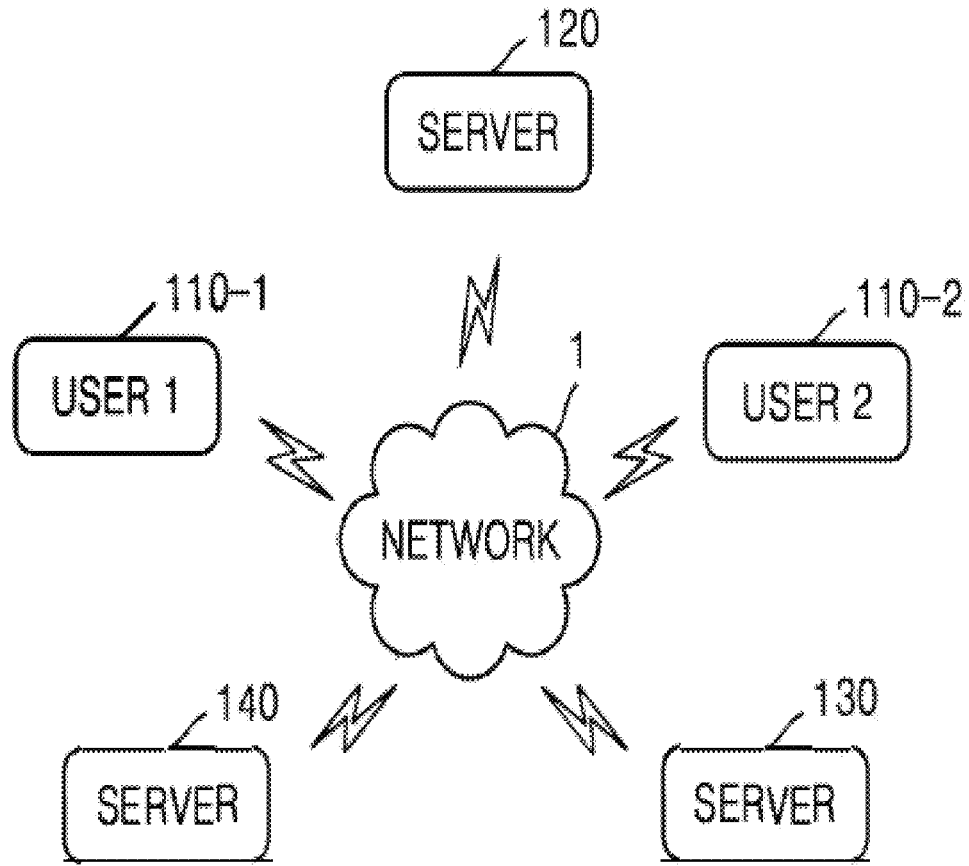
FIG. 1 is a diagram showing an example of an operating environment of a system according to an embodiment of the present disclosure.

In describing the embodiments of the present disclosure, when it is determined that a certain detailed description of known elements or functions may obscure the subject matter of the embodiments of the present disclosure, the detailed description is omitted. In the drawings, elements that are irrelevant to the embodiments of the present disclosure are omitted, and like reference numerals are affixed to like elements.

In the embodiments of the present disclosure, when an element is referred to as being "connected to", "coupled to" or "linked to" another element, it can be directly connected to the other element, and intervening elements may be present. Additionally, the term "comprises" or "includes" when used in this specification, specifies the presence of stated element but does not preclude the presence or addition of one or more other elements unless the context clearly indicates otherwise.

In the embodiments of the present disclosure, the terms "first", "second" and the like are used to distinguish one element from another, and are not intended to limit the order or importance between the elements unless otherwise specified. Accordingly, in the scope of the embodiments of the present disclosure, a first element in an embodiment may be referred to as a second element in other embodiment, and likewise, a second element in an embodiment may be referred to as a first element in other embodiment.

In the embodiments of the present disclosure, the distinguishable elements are for the purpose of clearly describing the features of each element, and it does not necessarily mean that the elements are separated. That is, a plurality of elements may be integrated into a single hardware or software, and a single element may be distributed into a plurality of hardware or software. Accordingly, unless the context clearly indicates otherwise, the integrated or distributed embodiment is included in the scope of the embodiments of the present disclosure.

In the present disclosure, a network may be the concept including a wired network and a wireless network. In this instance, the network may refer to a communication network for data exchange between a device and a system and between devices, and is not limited to a specific network.

The embodiments described in the present disclosure may have aspects of entirely hardware, partly hardware and partly software, or entirely software. In the present disclosure, "unit", "device" or "system" refers to a computer related entity such as hardware, a combination of hardware and software or software. For example, in the present disclosure, the unit, module, device or system may include a process that is being executed, a processor, an object, an executable, a thread of execution, a program, and/or a computer, but is not limited thereto. For example, both an application running in a computer and the computer may correspond to the unit, module, device or system of the present disclosure.

Additionally, in the present disclosure, the device may be not only a mobile device such as a smartphone, a tablet PC, a wearable device and Head Mounted Display (HMD), but also a fixed device such as a PC or an electric appliance having a display function. Additionally, for example, the device may be a cluster in a car or an IoT (Internet of Things) device. That is, in the present disclosure, the device may refer to devices in which applications can work, and is not limited to a particular type. Hereinafter, for convenience of description, devices in which applications work are referred to as the device.

In the present disclosure, a communication method of the network is not particularly limited, and each element may not be connected by the same networking method. The network may include not only communication methods using communication networks (for example, a mobile communication network, a wired Internet, a wireless Internet, a broadcast network and a satellite network) but also local area wireless communication between devices. For example, the network may include any communication method for networking between objects, and is not limited to wired communication, wireless communication, 3G, 4G, 5G, or any other method. For example, the wired and/or wireless network may refer to a communication network by at least one communication method selected from the group consisting of Local Area Network (LAN), Metropolitan Area Network (MAN), Global System for Mobile Network (GSM), Enhanced Data GSM Environment (EDGE), High Speed Downlink Packet Access (HSDPA), Wideband Code Division Multiple Access (W-CDMA), Code Division Multiple Access (CDMA), Time Division Multiple Access (TDMA), Bluetooth, Zigbee, Wi-Fi, VoIP (Voice over Internet Protocol), LTE Advanced, IEEE802.16m, Wireless-MAN-Advanced, HSPA+, 3GPP Long Term Evolution (LTE), Mobile WiMAX (IEEE 802.16e), UMB (formerly EV-DO Rev. C), Flash-OFDM, iBurst and MBWA (IEEE 802.20) systems, HIPERMAN, Beam-Division Multiple Access (BDMA), Wi-MAX (World Interoperability for Microwave Access) and communication using ultrasonic waves, but is not limited thereto.

The elements described in various embodiments are not necessarily essential elements, and some of them may be optional elements. Accordingly, embodiments including a subset of elements described in the embodiments are also included in the scope of the embodiments of the present disclosure. Additionally, embodiments including the elements described in various embodiments and further including other elements are included in the scope of embodiments of the present disclosure.

Hereinafter, the embodiments of the present disclosure will be described in detail with reference to the accompanying drawings.

FIG. 1 is a diagram showing an example of an operating environment of a system according to an embodiment of the present disclosure. Referring to FIG. 1, a user device 110 and one or more servers 120, 130, 140 are connected via a network 1. FIG. 1 is provided to describe the present disclosure by way of illustration and the number of user devices or servers is not limited to the exemplary number of FIG. 1.

The user device 110 may be a fixed or mobile terminal implemented by a computer system. The user device 110 may include, for example, a smart phone, a mobile phone, a navigation, a computer, a laptop computer, a terminal for digital broadcast, Personal Digital Assistant (PDA), Portable Multimedia Player (PMP), a tablet PC, a game console, a wearable device, a smart ring, an Internet of Things (IoT) device, a virtual reality (VR) device and an augmented reality (AR) device. For example, in the embodiments, the user device 110 may, in substance, refer to one of various physical computer systems that can communicate with the servers 120 to 140 via the network 1 using a wireless or wired communication method.

Each server may be implemented as a computer device or a plurality of computer devices that provide instructions, code, files, content and services by communication with the user device 110 via the network 1. For example, the server may be a system that provides each service to the user device 110 having made connection via the network 1. As a more specific example, the server may provide intended services (for example, providing information) to the user device 110 through an application as a computer program installed and running on the user device 110. As another example, the server may distribute files for installation and execution of the above-described application to the user device 110, receive user input information and provide the corresponding services.

Figure 2:
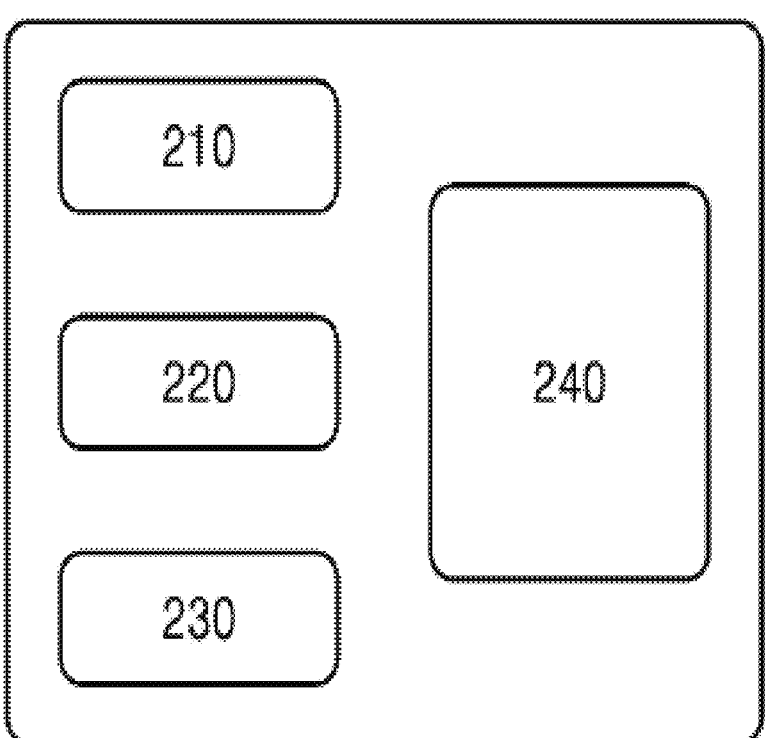
FIG. 2 is a block diagram illustrating an internal configuration of a computing device 200 in an embodiment of the present disclosure.

FIG. 2 is a block diagram illustrating the internal configuration of a computing device 200 in an embodiment of the present disclosure. The computing device 200 may be applied to one or more user devices 110-1, 110-2 or servers 120 to 140 described above with reference to FIG. 1, and each device and each server may have the same or similar internal configuration with the addition or exception of some components.

Referring to FIG. 2, the computing device 200 may include a memory 210, a processor 220, a communication module 230 and a transmitter/receiver 240. The memory 210 is a non-transitory computer-readable recording medium, and may include a non-volatile mass storage device such as Random Access Memory (RAM), Read Only Memory (ROM), disk drive, solid state drive (SSD) and flash memory. Here, the non-volatile mass storage device such as ROM, SSD, flash memory and disk drive may be a permanent storage device that is different from the memory 210 and included in the above-described device or server. Additionally, the memory 210 may store an operating system and at least one program code (for example, code for a browser installed and running on the user device 110 or an application installed on the user device 110 to provide a specific service). These software components may be loaded from other computer-readable recording medium than the memory 210. The other computer-readable recording medium may include computer-readable recording media such as floppy drive, disk, tape, DVD/CD-ROM drive and memory card.

In another embodiment, the software components may be loaded onto the memory 210 through the communication module 230 rather than the computer-readable recording medium. For example, at least one program may be loaded onto the memory 210 based on the computer program (for example, the above-described application) installed by the files provided by developers or a file distribution system (for example, the above-described server) that distributes the installer files of the application via the network 1.

The processor 220 may be configured to execute the instructions of the computer program by the basic operations, i.e., arithmetic and logic operations and input and output operations. The instructions may be provided to the processor 220 by the memory 210 or the communication module 230. For example, the processor 220 may be configured to execute the received instructions according to the program code stored in the recording device such as the memory 210.

The communication module 230 may provide a function for communication between the user device 110 and the servers 120 to 140 via the network 1, and may provide a function for communication between each of the device 110 and/or the servers 120 to 140 and another electronic device.

The transmitter/receiver 240 may be a means for interfacing with an external input/output device (not shown). For example, the external input device may include a keyboard, a mouse, a microphone and a camera, and the external output device may include a display, a speaker and a haptic feedback device.

Additionally, in other embodiments, the computing device 200 may include a larger number of components than the components of FIG. 2 according to the nature of a device to which the computing device 200 is applied. For example, when the computing device 200 is applied to the user device 110, the computing device 200 may include at least some of the above-described input/output devices or may further include other components such as a transceiver, a Global Positioning System (GPS) module, a camera, various types of sensors and a database. As a more specific example, when the user device is a smartphone, the computing device 200 may further include a variety of components generally included in the smartphone, for example, an acceleration sensor, a gyro sensor, a camera module, a variety of physical buttons, buttons using a touch panel, an input/output port and a vibrator for vibration.

Figure 3:
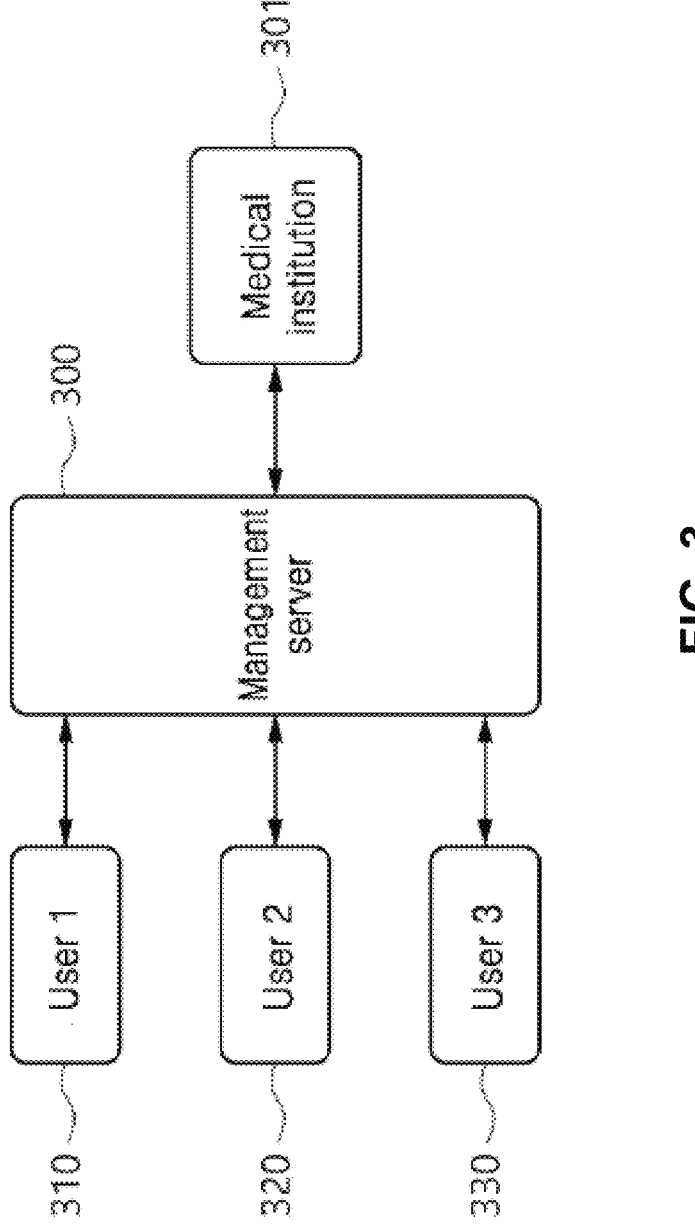
FIG. 3 shows a system environment in which a method for evaluating health status using skeleton models according to an embodiment of the present disclosure is performed.

FIG. 3 shows a system environment in which a method for evaluating health status using skeleton models according to an embodiment of the present disclosure is performed. Referring to FIG. 3, a health management server 300 may communicate with one or more user devices 310 to 330, and the health management server 300 also may communicate with a medical institution server 301. The health management server 300, the user devices 310 to 330 and the medical institution server 301 of FIG. 3 may be implemented as the computing device described in FIG. 2. Although FIG. 3 shows three user devices, the number of user devices is not limited thereto and may be more than three or less than three.

In an embodiment, the health management server 300 may provide a variety of standard motion images to the user device, and may receive a user motion image from the user device, conduct analysis, generate health information based on the user motion and provide the health information to the user device or the medical institution server. Alternatively, the health management server 300 may provide the user motion image to the medical institution server 301 after processing or analysis, and receive clinical determination information from the medical institution server, then additionally analyze the user motion image.

In an embodiment, the health management server 300 may provide the user device 310 with a standard motion image of a trainer making a standard motion. The following description is made based on one user device 310 by way of example, but the same procedure may be performed on other user devices.

Figure 4:
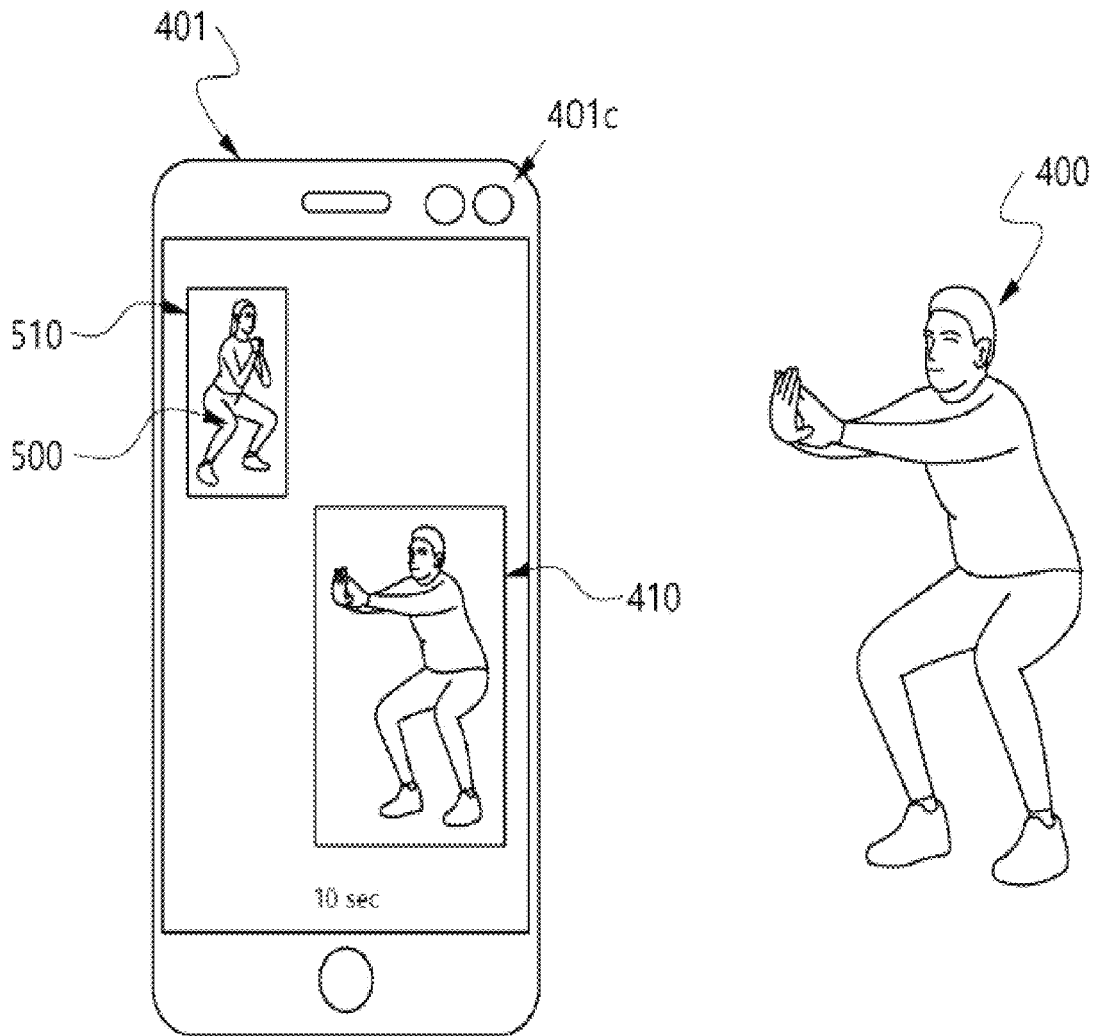
FIG. 4 shows a user taking a pose to imitate a standard motion according to an embodiment of the present disclosure.

FIG. 4 shows the user taking a pose to imitate the standard motion according to an embodiment of the present disclosure. Referring to FIG. 4, the user 400 may imitate the standard motion image 510 of the trainer 500 making the standard motion using the user device 401. The action of the user 400 may be captured by a camera 401*c* of the user device 401 and recorded in the form of an image.

In an example, the image captured by the camera 401*c* may come in various types, for example, a color image, a depth image and a color and depth image. Thus, the camera 401*c* may include a depth camera or may be a stereo camera, but is not limited thereto.

In the present disclosure, this image is referred to as the user motion image 410. The user motion image 410 may or may not be displayed on a display unit of the user device.

The reproduction of the standard motion image and the capture of the user motion may be carried out in the user device through an application or a web service provided by the health management server 300. Accordingly, the health management server may possess the standard motion image as well as the user motion image, information before and after the user motion and basic information (age, gender, underlying disease, pattern of life, etc.) associated with the user.

Although FIG. 4 shows that the standard motion is a pose of hands clasped in front of chest, legs apart and knees bent, a variety of standard motions may be provided to evaluate the user's health status. The health management server 300 may receive the user motion image for the user motion of the user imitating the standard motion from the user device 310.

Subsequently, the health management server 300 may calculate similarity between the standard motion and the user motion by comparing the user motion image with the standard motion image. Subsequently, the health management server 300 may evaluate the user's health status based on the calculated similarity. For example, the health management server 300 may evaluate motor ability, cognitive ability and physical ability of the user by comparing the user motion with the standard motion, but is not limited thereto.

Figure 5:
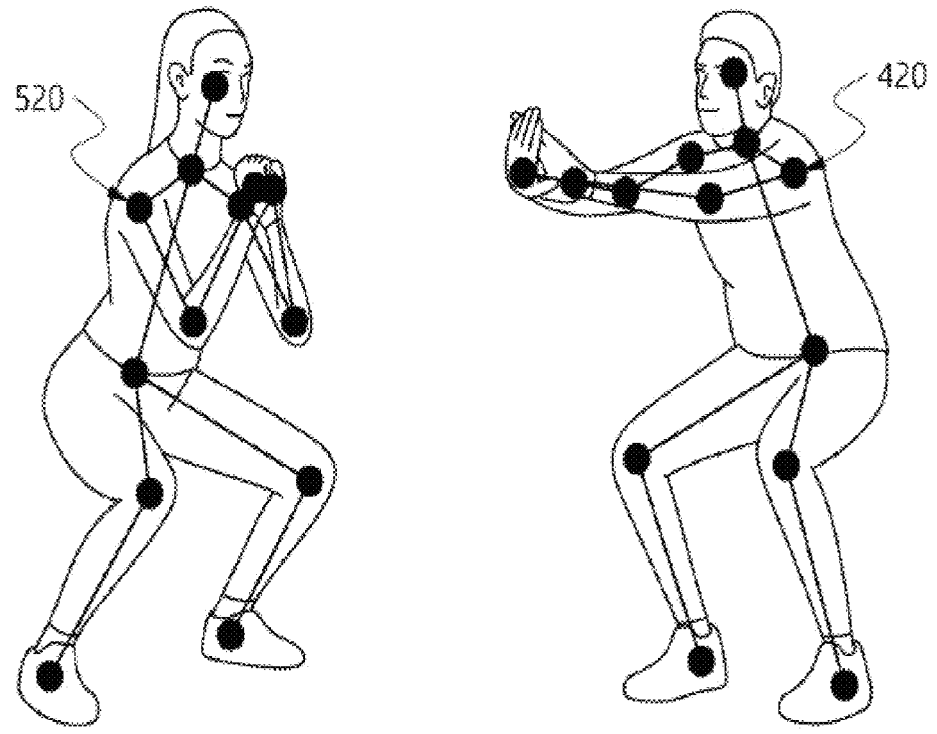
FIG. 5 shows a skeleton model extracted for each of a trainer 500 and a user 400 in a standard motion image and a user motion image according to an embodiment of the present disclosure.

In an embodiment, the health management server 300 may calculate the above-described similarity by applying a skeleton model of an object in the image. FIG. 5 shows the skeleton model extracted for each of the trainer 500 and the user 400 in the standard motion image and the user motion image according to an embodiment of the present disclosure. The skeleton model may be displayed to the user or may not be displayed to the user.

In an example, the health management server 300 may extract the skeleton motion model for the trainer and the user in the standard motion image or the user motion image using a learning model that locates joints or other body parts based on human body images. The skeleton motion model may include a plurality of nodes (feature points for each body part). The type of body part to which the node is assigned and the number of nodes may be variously set as necessary, but preferably 24 nodes may be applied to each joint part. However, for simplicity and clarity of illustration, a smaller number of nodes is shown in the drawings.

Additionally, in the present disclosure, the skeleton motion model may be placed on a 2-dimensional (2D) space or a 3-dimensional (3D) space. This may be determined according to the type of image acquired. That is, because the view of the standard motion image and the view of the user motion image may not match accurately, it is necessary to match the view of the 3D skeleton motion model of at least one of the standard motion image or the user motion image to the skeleton motion model of the other image. In this case, the health management server 300 may change the view of the skeleton motion model in 3D to the view of the skeleton motion model in 2D to compare the two skeleton motion models.

Specifically, in an embodiment, the health management server 300 may perform the step of acquiring the trainer skeleton motion model for the trainer making the standard motion in the standard motion image. Additionally, the health management server 300 also may perform the step of acquiring the user skeleton motion model for the user making the user motion in the user motion image. Subsequently, the health management server 300 may calculate the similarity by comparing the feature points for each corresponding body part between the trainer skeleton motion model and the user skeleton motion model. Here, the feature points for each body part may be the nodes of the skeleton motion models.

In an example, the similarity is Euclidean Distance and may be determined based on a predetermined formula for Euclidean Distance. That is, the similarity may be measured by comparing the positions of the corresponding body part feature points between the user skeleton motion model and the trainer skeleton motion model. In this instance, the similarity may be indicated in %.

For example, to compare the two skeleton models, a distance between the corresponding nodes in a plane where the two skeleton models are projected or overlap may be calculated.

Figure 6A:
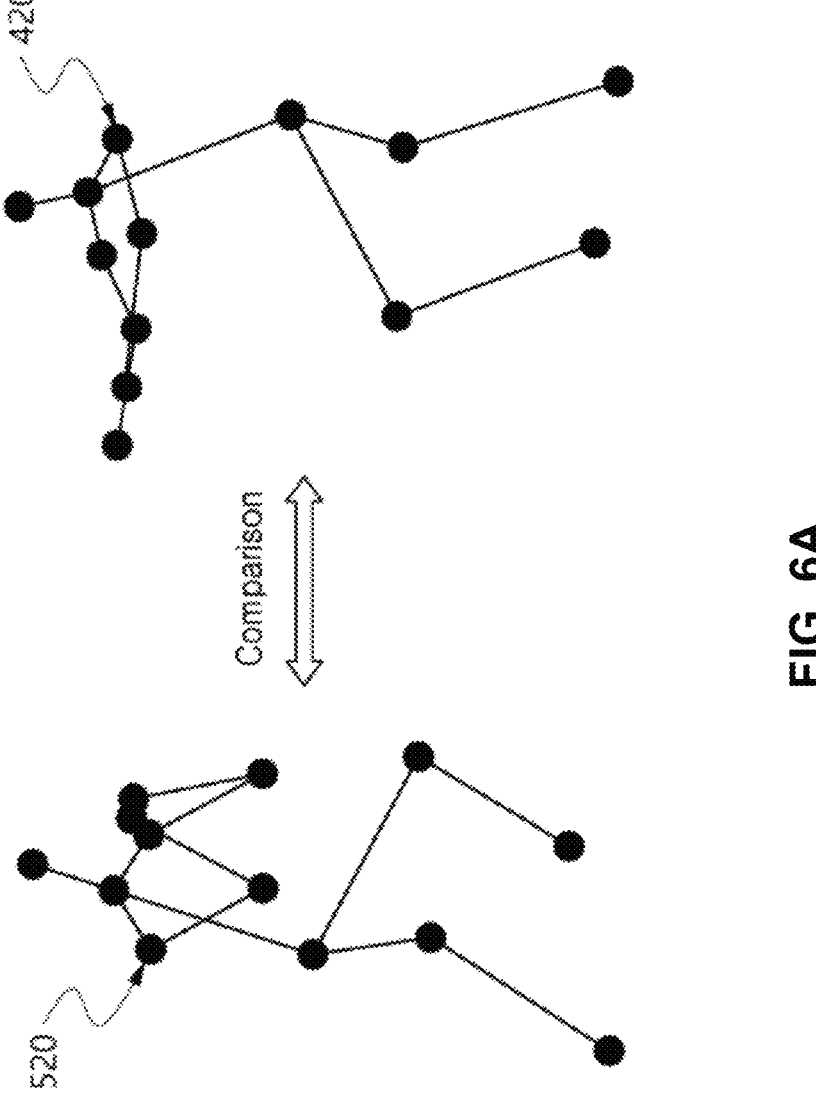
FIGS. 6A, 6B and 6C illustrate the comparison of a trainer skeleton motion model and a user skeleton motion model to calculate similarity in the present disclosure.
Figure 6B:
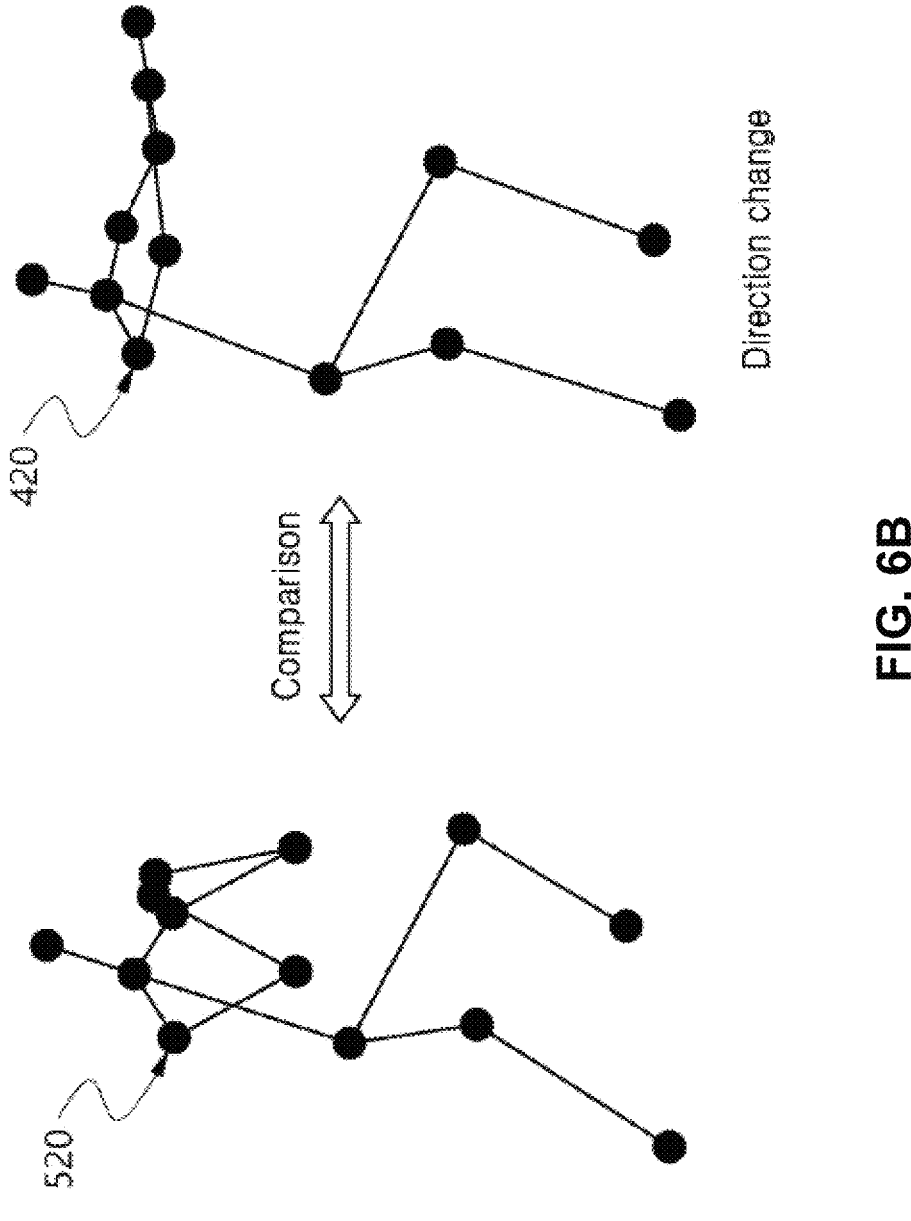

FIGS. 6*a* and 6*b* illustrate the comparison of the trainer skeleton motion model and the user skeleton motion model to calculate the similarity in the present disclosure. Referring to FIG. 6A, the health management server 300 may calculate the similarity between the trainer skeleton motion model 520 and the user skeleton motion model 420 based on the position of each node of the two models. Meanwhile, as mentioned above, the view of the user motion image may be different from the view of the standard motion image. In this case, to compare the positions of the nodes of the skeleton motion models in 2D plane, it is necessary to match the two skeleton models. The following description is made based on the user skeleton motion model modified to match the trainer skeleton motion model, but on the contrary, the trainer skeleton motion model may be modified to match the user skeleton motion model.

Referring to FIG. 6B, the health management server 300 may rotate the user skeleton motion model 420 to match the view to the trainer skeleton motion model. To enable the rotation, the user skeleton motion model may be a 3D model.

In an example, the trainer's physical conditions and the user's physical conditions may be different from each other. In this case, when comparing the two skeleton models as they are, the similarity may be high regardless of whether the poses match or mismatch. To solve this problem, it is necessary to match the size of the two skeleton models.

Figure 6C:
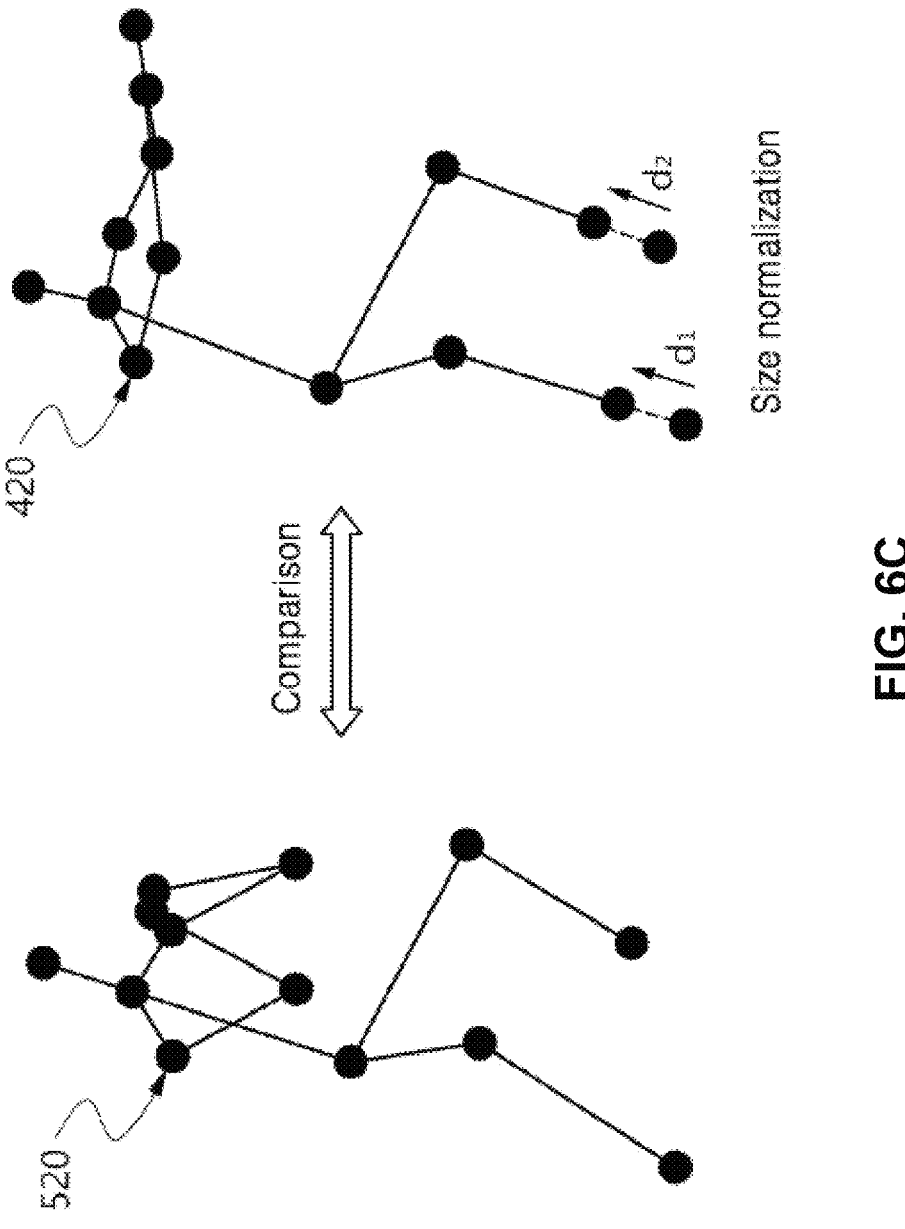

Referring to FIG. 6C, the health management server 300 may perform normalization to match the scale (size) of the user skeleton motion model 420 to the trainer skeleton motion model 520. Specifically, FIG. 6C shows that when the user has longer legs, the user's ankle-knee distance may be adjusted to match the trainer's physical condition. Accordingly, the knee-ankle distance of each leg may be reduced by d1 and d2.

The normalization process described in FIGS. 6A to 6C may be applied to any one of the two skeleton models or both.

Figure 7:
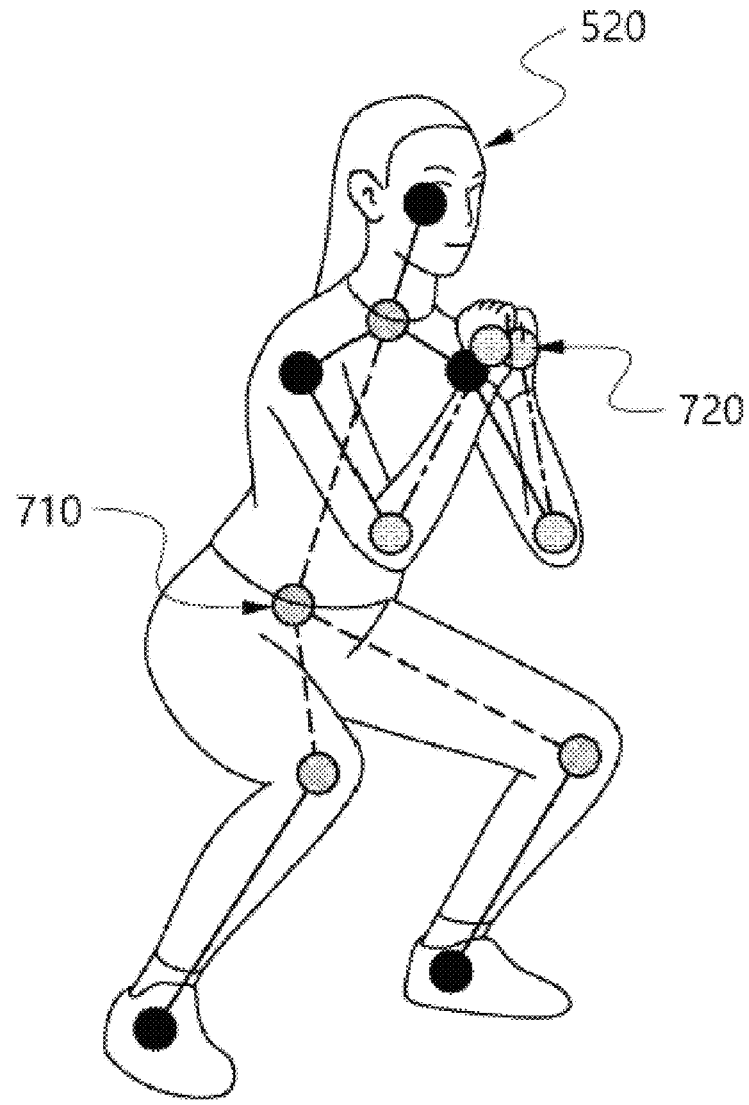
FIG. 7 is a diagram illustrating a weight per body part according to an embodiment of the present disclosure.

FIG. 7 is a diagram illustrating the weight per body part according to an embodiment of the present disclosure. Referring to FIG. 7, in an example, in calculating the similarity by comparing the feature points for each body part, the health management server 300 may fetch the weight per body part for the standard motion from the database, and apply the weight per body part to the similarity calculation. That is, some body parts may have high importance and some body parts may have low importance according to the type of standard motion. Referring to FIG. 7, the corresponding standard motion may have high importance in position and angle of neck and waist nodes and knee nodes (reference numeral 710), and low importance in position and angle of elbows and wrists (reference numeral 720). Based on this importance difference, the weight for the body part for each standard motion may be reflected on the similarity calculation.

TABLE 1 is a table showing the weight values for the body parts for each standard motion by way of example, and node n indicates each body part. For example, node 3 may be the right elbow, and node 5 may be the right shoulder, but this is provided by way of example. Additionally, in TABLE 1, the values of the weights 3, 2, 1 are provided by way of example.

TABLE 1

| Standard motion | Weight 3 | Weight 2 | Weight 1 |
|---|---|---|---|
| Standard motion 1 | Node 3, Node 5 | | |

TABLE 1-continued

| Standard motion | Weight 3 | Weight 2 | Weight 1 |
|---|---|---|---|
| Standard motion 2 | | Node 1, Node 14 | |
| Standard motion 3 | Node 5, Node 12 | | Node 2, Node 3, Node 4 |
| Standard motion 4 | | Node 8, Node 9 (cognitive impairment A) Node 10, Node 12 (cognitive impairment B) | Node 2-Node 4- Node 6 (angle) |

Figure 8:
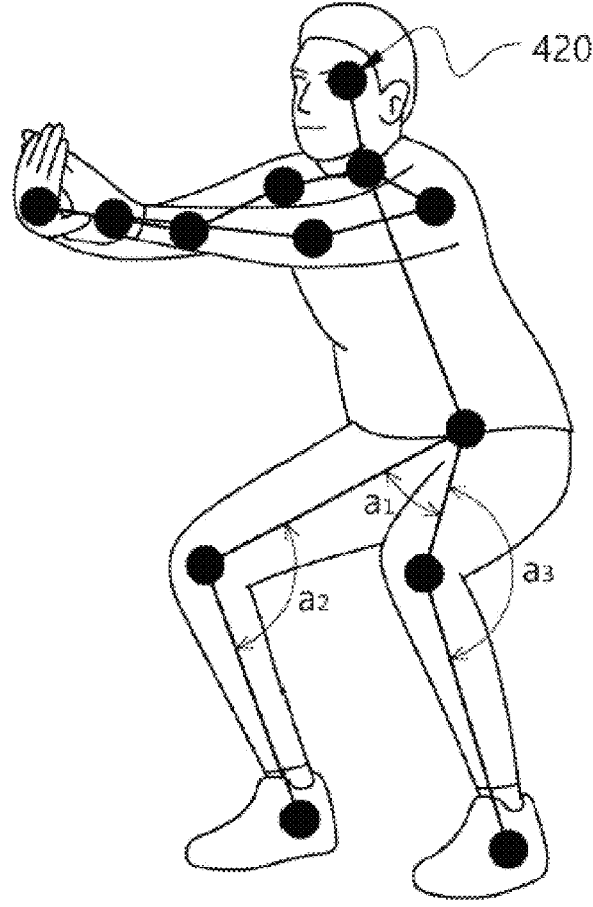
FIG. 8 shows angles of body parts (pose) formed by nodes according to an embodiment of the present disclosure.

The weight per body part is assigned for each standard motion, but may be subdivided for each cognitive impairment. For example, in standard motion 4, to evaluate cognitive impairment A, the weight may be assigned to node 8 and node 9, but to evaluate cognitive impairment B, in standard motion 4, the weight may be assigned to node 10 and node 12. Additionally, the similarity described herein may be determined using the distance between the corresponding nodes and further using an angle formed by three or more nodes. Referring to FIG. 8, values of an angle (a1) between two legs, an angle (a2) of right knee bending and an angle (a3) of left knee bending in the user skeleton motion model may be compared with angles of the corresponding body parts of the trainer skeleton motion model.

Additionally, because the skeleton motion models have a temporal element, the temporal element may be considered when calculating the similarity. For example, when a difference of 2 cm is maintained for 1 sec and a difference of 0.5 cm is maintained for 5 sec, in the latter case, a lower similarity value may be calculated.

In an embodiment, the health management server 300 may evaluate the user's health status based on the above-described similarity calculation. Here, evaluating the health status is evaluating the exhaustion of physical strength or cognitive impairment level of the user.

In an example, the cognitive impairment level may be determined according to the level of similarity calculated. That is, when similarity for a specific standard pose is lower than a predetermined value, a probability of having cognitive impairment corresponding to the specific standard pose may be calculated. More specifically, evaluation may be conducted based on behavioral feature data in cognitive impairment for each standard motion. That is, when the ability to imitate the standard motion is less than a predetermined level, the cognitive impairment probability may be given, and for more accurate determination, behavioral feature data of cognitive impairment patients for each standard motion may be further used.

For example, the behavioral feature data may be data of nodes representative of behavioral features of patients for each cognitive impairment type for each standard motion as shown in TABLE 2 below. The weight per body part for the standard motion may be organized in database and stored in the health management server 300 or an external device.

TABLE 2

| Standard motion | Type of cognitive impairment | Behavioral feature in cognitive impairment | Node detected |
|---|---|---|---|
| Standard motion 1 | A | Extending arms forward | Node 3, Node 5, Node 7 |

TABLE 2-continued

| Standard motion | Type of cognitive impairment | Behavioral feature in cognitive impairment | Node detected |
|---|---|---|---|
| Standard motion 2 | A | Failing to maintain for 2 seconds or more | Node 4, Node 6 |
| Standard motion 3 | B | Similarity of less than 60% (i.e., failing to imitate the posture when seen by the naked eye) | Node 3, Node 10, Node 13 |
| Standard motion 4 | B | Failing to maintain for 3 seconds or more | Node 4, Node 6 |

% value of similarity may be determined by an evaluator's input, or determined according to a predefined criterion, or continuously updated through the artificial intelligent learning model. Additionally, for example, in evaluating the user's health status, the health management server 300 may evaluate the exhaustion of physical strength of the user. Specifically, the exhaustion of physical strength is used to identify the increased quantity of motion due to an unnecessary motion or pose when imitating the standard motion.

For example, the exhaustion of physical strength may be determined based on the sum of movement trajectories of the feature points for each body part of the user skeleton motion model and a predefined physical strength exhaustion evaluation weight for the amount of movement for each body part. That is, when the user imitates the standard motion of standing up from a sitting position, in the case in which the user turns (rotates) his/her arms, the exhaustion of physical strength may be calculated, taking into account the movement trajectories of the nodes of both arms. Additionally, in another example, the weight for the amount of movement for each body part may be assigned. Specifically, the weight for the amount of movement for each body part includes a larger physical strength exhaustion weight assigned for the leg raising motion because the leg raising motion consumes more energy than the arm raising motion. Additionally, because pushing the thigh backward consumes more energy than pushing the thigh forward, in order to reflect this difference, the above-described exhaustion of physical strength weight per body part may be used.

Referring back to FIG. 3, the health management server 300 may receive the user motion image from a plurality of user devices. The plurality of received user motion images may be real-time images or images captured at different times.

The health management server 300 may display the plurality of received user motion images on a display device. Here, the display device may be the user device or a display device of the medical institution 301. The health management server 300 may provide the corresponding image to the user or the medical institution through a web or an app. Hereinafter, the health management server 300 providing the plurality of user motion images and the standard motion image to the medical institution server 301 will be described. More specifically, providing the processing and analysis results of each image to the medical institution server together with the images will be described. Based on the provided information, a medical specialist may see the motion images for the plurality of users and use them for diagnosis.

Figure 9:
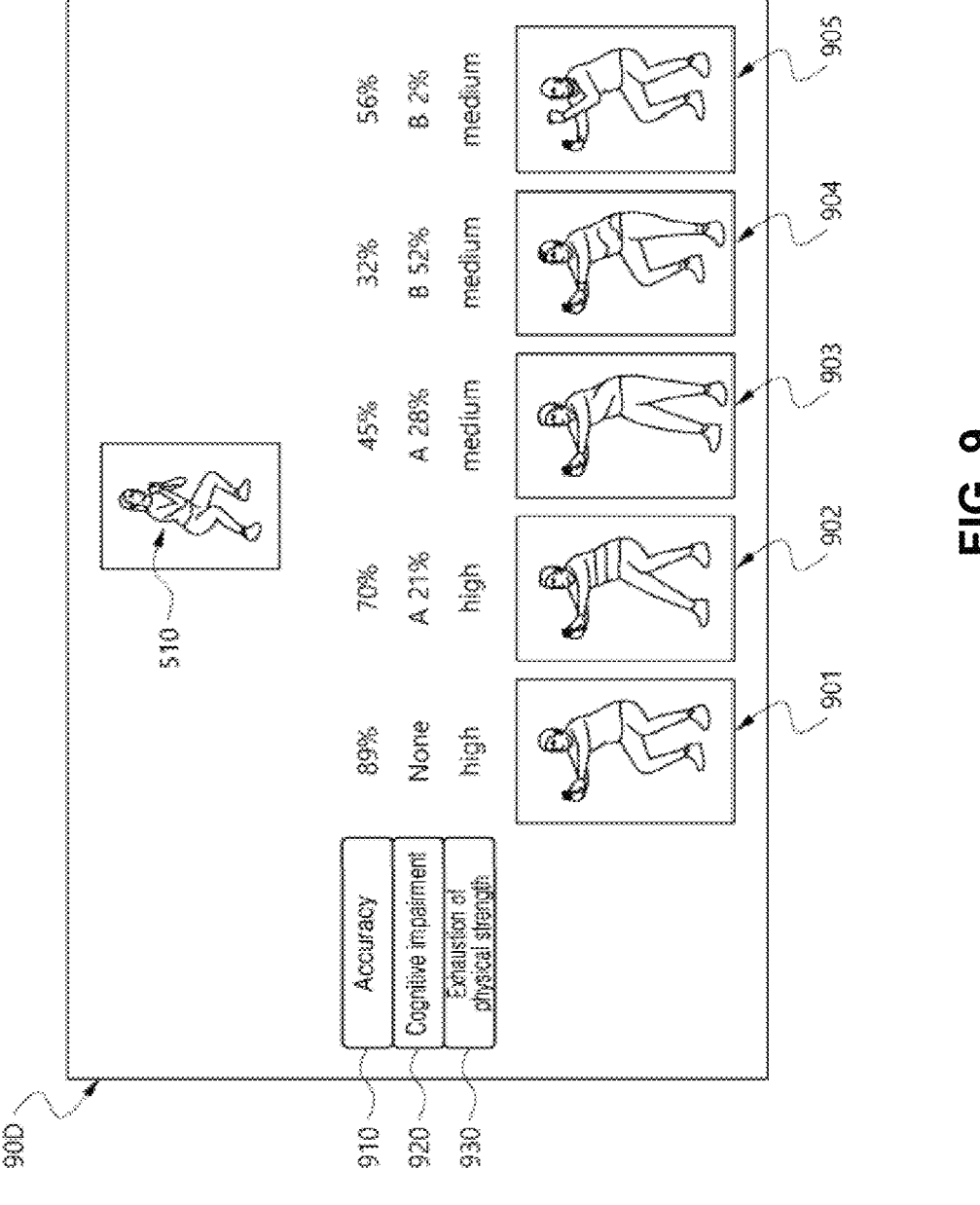
FIG. 9 shows a plurality of user motion images provided by a health management server 300 and their analysis results according to an embodiment of the present disclosure.

FIG. 9 shows the plurality of user motion images provided by the health management server 300 and their analysis results according to an embodiment of the present disclosure. Referring to FIG. 9, the standard motion image 510 is displayed, and along with this, the plurality of user motion images 901 to 905 are displayed on the display device 90D.

The health management server 300 may calculate the similarity between each of the plurality of user motions in the plurality of received user motion images and the standard motion. This step has been described above in detail. Through the similarity calculation and subsequent evaluation, the similarity (accuracy) 910 to the standard motion for each user motion may be displayed, the presence or absence of cognitive impairment and the type and probability 920 of cognitive impairment may be displayed, and the exhaustion of physical strength 930 may be displayed. The doctor may see and compare the motions of the plurality of patients through this display.

Figure 10:
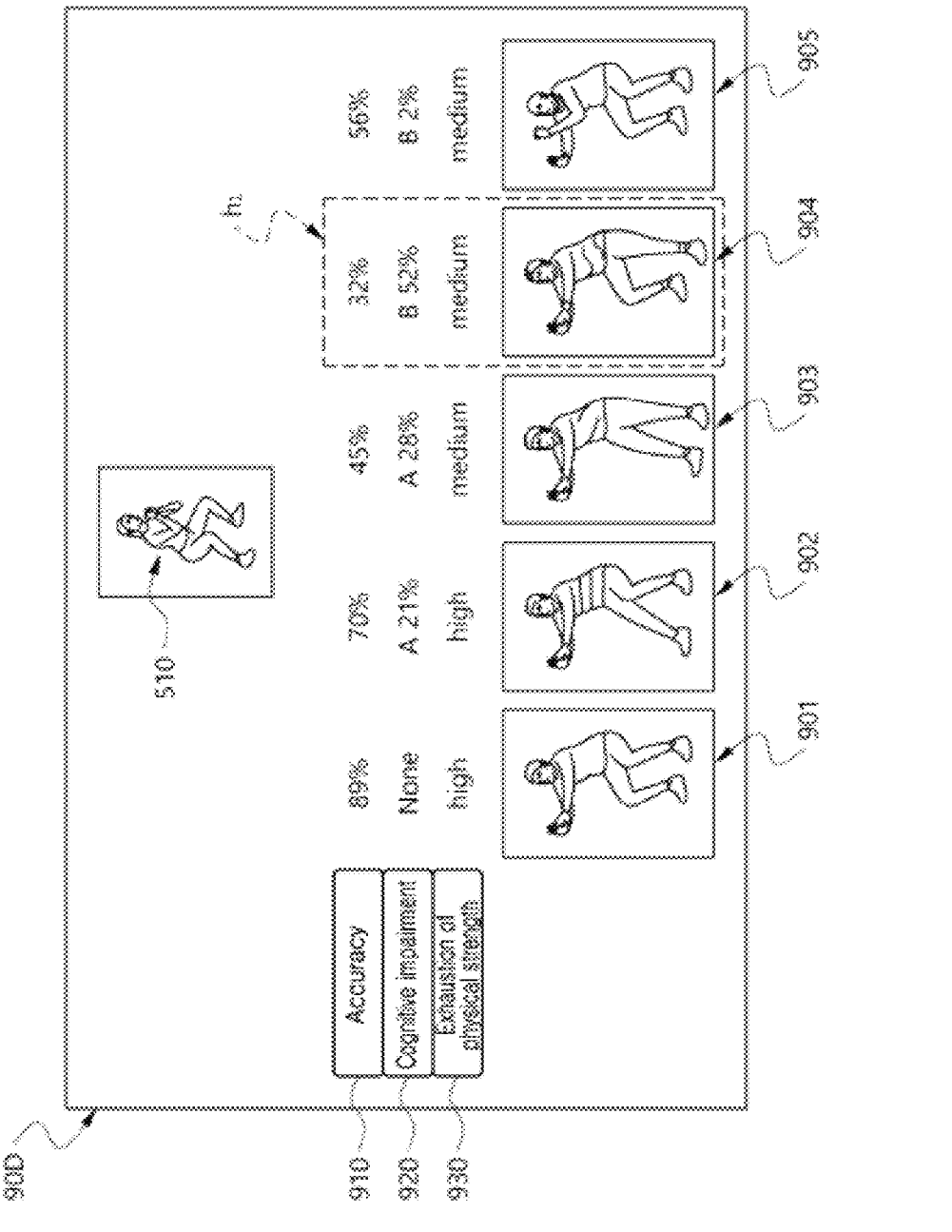
FIG. 10 illustrates the highlighting of a user motion image having low similarity to a standard motion in an embodiment of the present disclosure.

FIG. 10 illustrates the highlighting of the user motion image having low similarity to the standard motion in an embodiment of the present disclosure.

In an example, the health management server 300 may highlight at least one of the plurality of user motion images displayed on the display device based on the calculated similarity. Specifically, as shown in FIG. 10, the health management server 300 may highlight (h1) a predetermined number of user motion images having the calculated similarity in a lower or higher range than the predetermined criterion among the plurality of user motion images. Accordingly, the doctor may quickly identify the user who has difficulty in imitating the standard motion. Specifically, the doctor may make quick clinical determination by seeing all the highlighted physical activities of the user with the naked eye. Without this guide, there is inconvenience of having to seeing every image for the total reproduction time.

Figure 11:
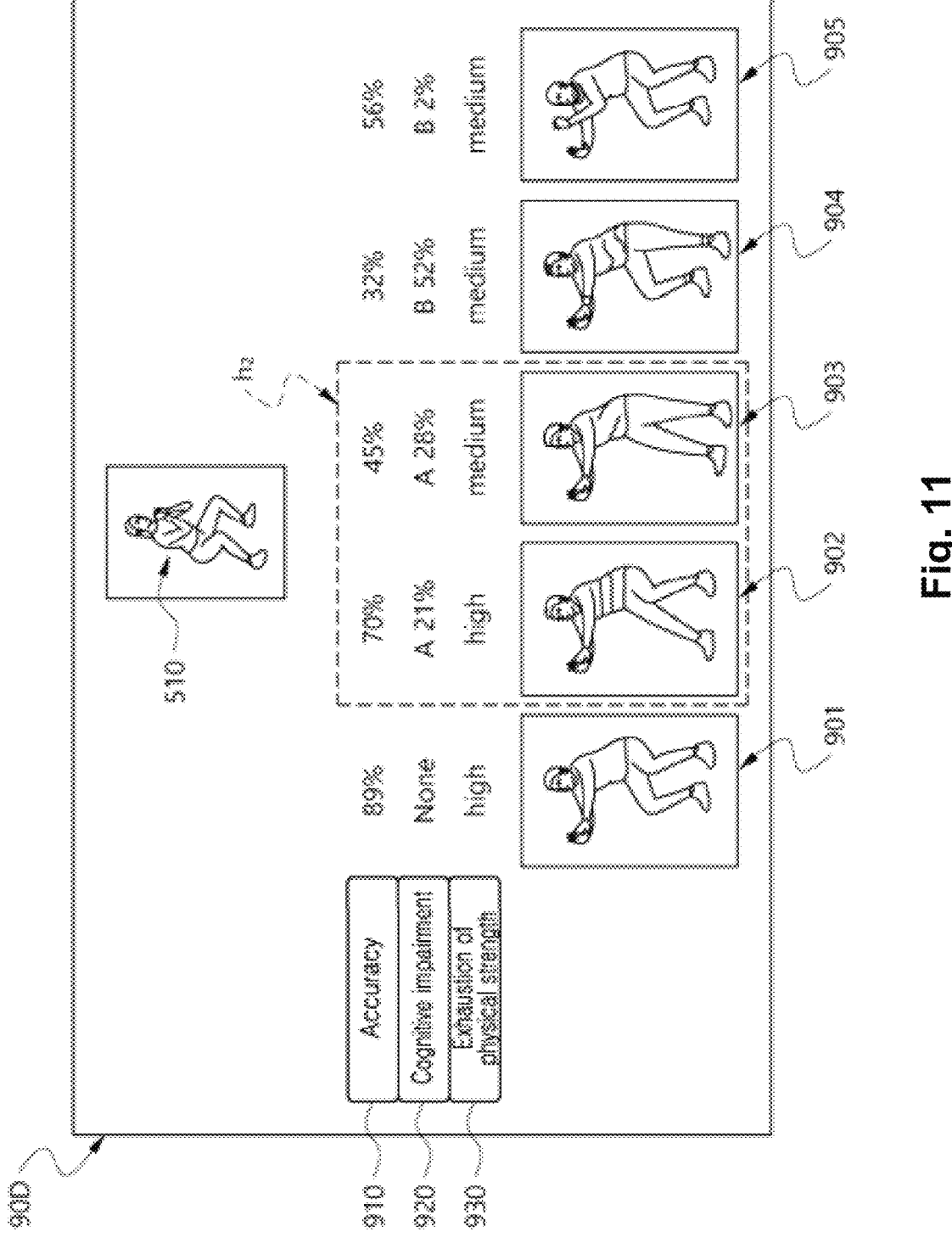
FIG. 11 illustrates the grouping and displaying of two or more relevant user motion images according to an embodiment of the present disclosure.

FIG. 11 illustrates the grouping and displaying of two or more relevant user motion images according to an embodiment of the present disclosure. In an example, the health management server 300 may calculate the similarity between users by comparing the skeleton motion models for the plurality of user motions, and group the plurality of user motion images based on the calculated similarity between users. Subsequently, the grouped user motion images may be differently displayed. That is, the user motion images determined to have the same cognitive impairment according to data may be grouped and displayed. In FIG. 11, the highlight is indicated by the dotted box, but this is provided by way of illustration and a variety of visual effects such as labels or changes in shadow or image size may be included in the above-described 'highlight'. Additionally, in an example, in calculating the similarity between users by comparing the skeleton motion models for the plurality of user motions, the health management server 300 may not apply the weight per body part for the standard motion. When the weight per body part for the standard motion is applied, it may be possible to determine cognitive impairment that matches the standard motion quickly and accurately. However, to find an unknown disorder or activity pattern of the user, not applying the weight may be helpful. For example, in the case that the weight per body part is not applied, when imitating standard motion A, a user group having a backward head tilt pattern may be found, and the doctor may make clinical determination by conducting naked-eye evaluation. For example, accordingly, a conclusion that the users have cognitive impairment C may be made by clinical determination.

Figure 12:
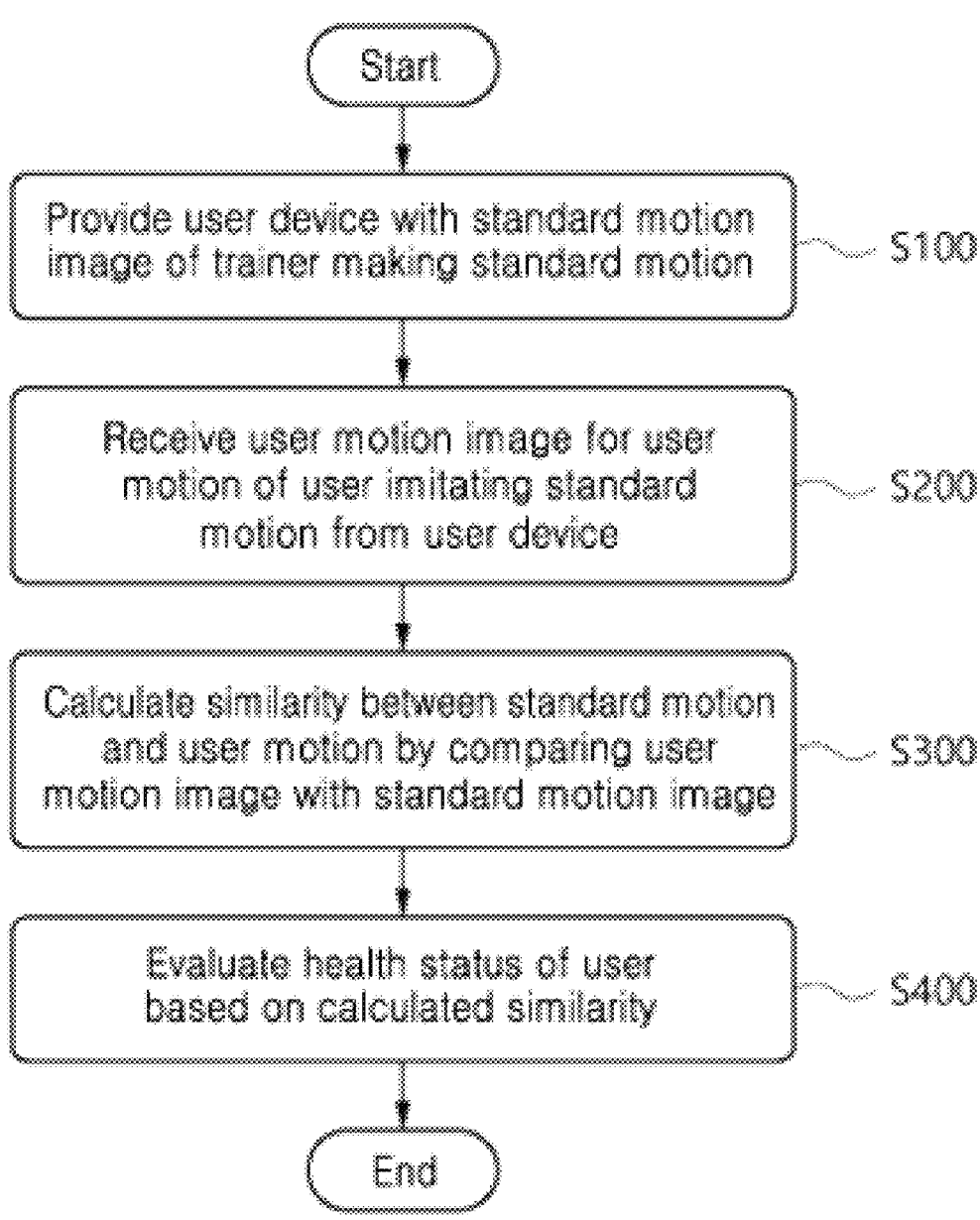
FIG. 12 is a flowchart of a method for evaluating health status using skeleton models according to an embodiment of the present disclosure.

FIG. 12 is a flowchart of a method for evaluating health status using skeleton models according to an embodiment of the present disclosure. The evaluation method may be performed by the above-described health management server. Referring to FIG. 12, the method for evaluating health status using skeleton models may include the steps of providing the user device with the standard motion image of the trainer making the standard motion (S100), receiving the user motion image for the user motion of the user imitating the standard motion from the user device (S200), calculating the similarity between the standard motion and the user motion by comparing the user motion image with the standard motion image (S300), and evaluating the user's health status based on the calculated similarity (S400). Here, the step of calculating the similarity (S300) may include the steps of acquiring the trainer skeleton motion model for the trainer making the standard motion in the standard motion image, acquiring the user skeleton motion model for the user making the user motion in the user motion image, and calculating the similarity by comparing the feature points for each corresponding body part between the trainer skeleton motion model and the user skeleton motion model, wherein the feature points for each body part may be the nodes of the skeleton motion models. More specifically, the step of calculating the similarity by comparing the feature points for each body part may include the steps of fetching the weight per body part for the standard motion from the database and applying the weight per body part to the similarity calculation. The step of evaluating the health status may include evaluating the exhaustion of physical strength or cognitive impairment level of the user, and the cognitive impairment level may be evaluated based on behavior feature data in cognitive impairment for each standard motion.

The above-described embodiments may be realized, at least in part, in a computer program and recorded on a computer-readable recording medium. The computer-readable recording medium that stores the program for realizing the embodiments includes any type of recording device in which computer-readable data is stored. Examples of the computer-readable recording medium include ROM, RAM, CD-ROM, magnetic tape and an optical data storage device. Additionally, the computer-readable recording medium is distributed over computer systems connected via a network, and may store and execute a computer-readable code in a distributed manner. Additionally, a functional program, code and a code segment for realizing this embodiment will be easily understood by persons having ordinary skill in the technical field to which this embodiment belongs.

While the present disclosure has been hereinabove described with reference to the embodiments shown in the drawings, this is provided for illustration purposes only and it will be appreciated by persons having ordinary skill in the art that a variety of modifications and variations may be made thereto. However, it should be noted that such modifications fall within the technical protection scope of the present disclosure. Therefore, it should be noted that the true technical protection scope of the present disclosure includes other embodiments, other examples and equivalents to the claims by the technical spirit of the appended claims.

INDUSTRIAL APPLICABILITY

The present disclosure may evaluate the user's motor imitation by comparing the user motion with the standard motion. The present disclosure may evaluate cognitive impairment or exhaustion of physical strength of the user by comparing the user motion with the standard motion. The present disclosure may compare the user motion with the standard motion using the skeleton models of the two motions.

The invention claimed is:

1. A method for evaluating health status using skeleton models, performed by a health management server, the method comprising the steps of:
   providing a user device with a standard motion image of a trainer making a standard motion;
   receiving a user motion image for a user motion of a user imitating the standard motion from the user device;
   calculating a similarity between the standard motion and the user motion by comparing the user motion image with the standard motion image; and
   evaluating the health status of the user based on the calculated similarity,
   wherein the step of calculating the similarity comprises the steps of:
      acquiring a trainer skeleton motion model for the trainer making the standard motion in the standard motion image;
      acquiring a user skeleton motion model for the user making the user motion in the user motion image; and
      calculating the similarity by comparing feature points for each corresponding body part between the trainer skeleton motion model and the user skeleton motion model, wherein the feature points for each body part are a plurality of nodes of the skeleton motion models,
   wherein the step of calculating the similarity by comparing the feature points for each body part comprises the steps of:
      fetching a weight per body part for the standard motion from a database; and
      applying the weight per body part to the similarity calculation,
   wherein the step of evaluating the health status comprises evaluating exhaustion of physical strength and cognitive impairment level of the user,
   wherein
      the standard motion includes a plurality of standard motions, and the cognitive impairment type includes a plurality of cognitive impairment types,
      the cognitive impairment level is evaluated based on behavior feature data in cognitive impairment type for each standard motion of the plurality of standard motions,
      the weight per body part is assigned for each standard motion of the plurality of standard motions, and the weight per body part is subdivided for each cognitive impairment type of the plurality of cognitive impairment types, and
      the behavior feature data is data of corresponding nodes of the plurality of nodes representative of behavioral features of the user for each cognitive impairment type for each standard motion.

2. The method for evaluating health status using skeleton models according to claim 1, wherein the exhaustion of physical strength is determined based on a sum of movement trajectories of the feature points for each body part of the user skeleton motion model; and a predefined physical strength exhaustion evaluation weight for an amount of movement for each body part.

3. The method for evaluating health status using skeleton models according to claim 1, wherein the method comprises the steps of:
   receiving the user motion image for each of a plurality of users from a plurality of user devices;

displaying the plurality of received user motion images on a display device;

calculating the similarity between each of the plurality of user motions in the plurality of received user motion images and the standard motion; and highlighting at least one of the plurality of user motion images displayed on the display device based on the calculated similarity.

4. The method for evaluating health status using skeleton models according to claim 3, wherein the step of highlighting comprises highlighting a predetermined number of user motion images having the calculated similarity in a lower or higher range than a predetermined criterion among the plurality of user motion images.

5. The method for evaluating health status using skeleton models according to claim 3, wherein the step of highlighting comprises the steps of:

calculating the similarity between users by comparing the skeleton motion models for the plurality of user motions;

grouping the plurality of user motion images based on the calculated similarity between users; and differently displaying the grouped user motion images.

6. The method for evaluating health status using skeleton models according to claim 5, wherein the step of calculating the similarity between users by comparing the skeleton motion models for the plurality of user motions comprises not applying the weight per body part for the standard motion.

7. A non-transitory computer readable recording medium including executable instructions, wherein the instructions, when executed by a processor, cause the processor to perform the method according to claim 1.

\* \* \* \* \*